United States Patent [19]
Peifer et al.

[11] Patent Number: 6,074,402
[45] Date of Patent: *Jun. 13, 2000

[54] CHANNEL MOUNTED ACTIVATING MECHANISM FOR AN ENDOSCOPIC LIGATOR

[75] Inventors: Rodney Peifer, Kernersville; Michael K. Simmons, Winston-Salem, both of N.C.

[73] Assignee: Wilson-Cook Medical Inc., Winston-Salem, N.C.

[ * ] Notice: This patent is subject to a terminal disclaimer.

[21] Appl. No.: 09/011,798

[22] PCT Filed: Sep. 6, 1996

[86] PCT No.: PCT/US96/14374

§ 371 Date: Feb. 13, 1998

§ 102(e) Date: Feb. 13, 1998

[87] PCT Pub. No.: WO97/08996

PCT Pub. Date: Mar. 13, 1997

Related U.S. Application Data

[63] Continuation of application No. 08/524,069, Sep. 6, 1995, Pat. No. 5,735,861.

[51] Int. Cl.⁷ .................................................. A61B 17/00
[52] U.S. Cl. ........................................... 606/139; 606/141
[58] Field of Search .................................... 606/139, 140, 606/141, 144

[56] References Cited

U.S. PATENT DOCUMENTS

| | | | |
|---|---|---|---|
| 5,163,948 | 11/1992 | Kummer | 606/152 |
| 5,174,276 | 12/1992 | Crockard | 128/4 |
| 5,197,649 | 3/1993 | Bessler et al. | 227/179 |
| 5,462,559 | 10/1995 | Ahmed | 606/140 |
| 5,735,861 | 4/1998 | Peifer et al. | 606/139 |

Primary Examiner—Michael Buiz
Assistant Examiner—Tina Pham
Attorney, Agent, or Firm—Woodard, Emhardt, Naughton, Moriarty & McNett Patent and Trademark Attorneys

[57] ABSTRACT

An activating mechanism (20) for activating an endoscopic ligator is disclosed. The activating mechanism (20) includes a mounting component (21) and an activating component (22) coupled thereto. The mounting component (21) inserts directly into the proximal opening of an operating channel of an endoscope and is dimensioned to fit within the operating channel to mount the mechanism (20) to the endoscope. The mounting component (21) includes a channel receiving an activation line of the ligating device which is threaded through the operating channel and the channel in the mounting component, and onto the activating component (22) of the activating mechanism (20). The activation line attaches to a spool (50) of the activating component (22). The activating component (22) further provides a drive pin (40) and a roller clutch (70) for setting the activating component (22) in an engaged or disengaged position and a knob (60) for rotating the drive pin (40). When the drive pin (40) is engaged with the roller clutch (70), the knob (60) can only rotate in one direction. When the drive pin (40) is in the disengaged position from the roller clutch (70), the knob (60) can rotate in either direction.

13 Claims, 21 Drawing Sheets

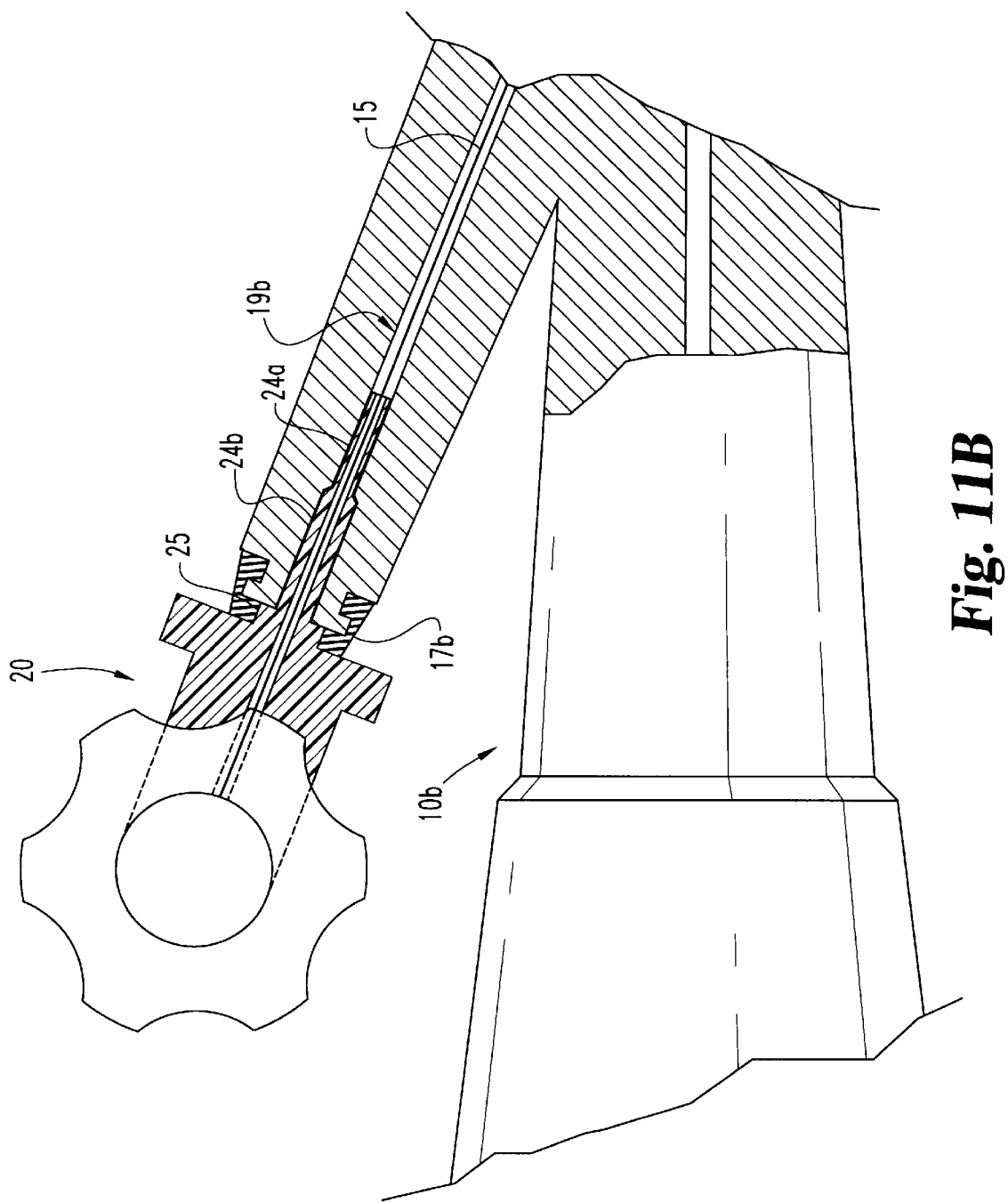

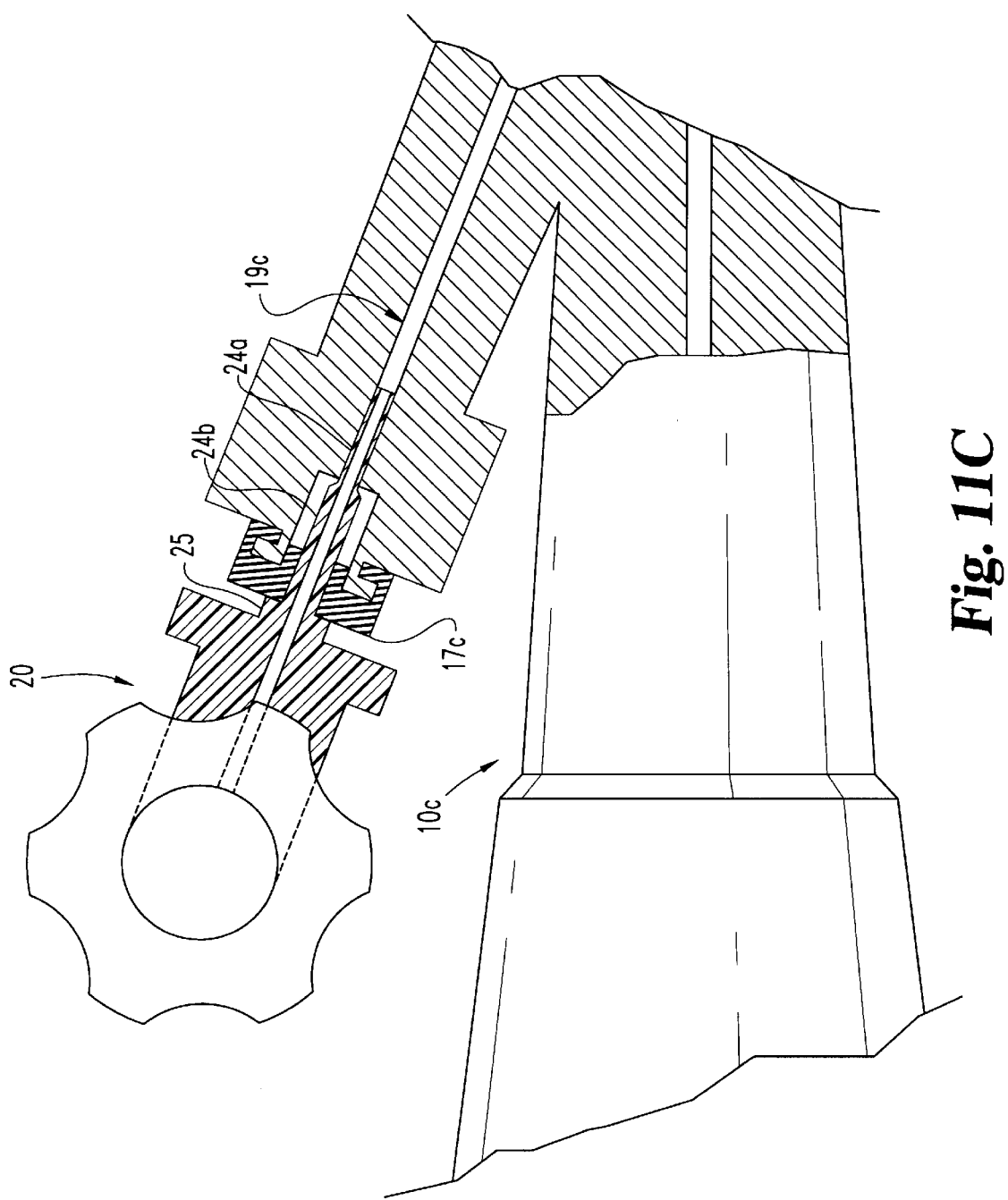

CHANNEL MOUNTED ACTIVATING MECHANISM FOR AN ENDOSCOPIC LIGATOR

This application is a continuation application of application Ser. No. 08/524,069 filed Sep. 6, 1995. Now U.S. Pat. No. 5,735,861.

BACKGROUND OF THE INVENTION

1. Field of the Invention

The invention relates to the field of endoscopic ligation. More particularly, the invention relates to devices which are used to activate an endoscopic ligator for ligating lesions within a hollow organ of the body.

2. Background

Endoscopic ligating devices which apply elastic rings over selected body tissue are well known in the prior art. The ligating device is typically activated by retracting a line (string, wire, or cable) that is attached to a ligator disposed at the distal or insertion end of an endoscope. The line is threaded through a working or operating channel of the endoscope to the proximal end of the instrument. In some prior devices, the ligator can be activated by manually pulling on the activating line. In other devices, mechanically assisted operation is provided by means of a hand operated reel or trigger, or a motor drive mechanism.

Pre-existing activating mechanisms have generally not been securely mountable to the endoscope, or easily and securely attachable to variously configured endoscopes, have not operated with satisfactory control and accuracy, and have been difficult to disconnect. Wherefore, there is a need for a new activating mechanism which overcomes these shortcomings of prior activating mechanisms.

SUMMARY OF THE INVENTION

The present invention provides a new and unique activating mechanism for an endoscopic ligator which mounts to a variety of endoscopes and operates to provide precise control to effectuate ligation. The device is easy and convenient to use, and can be simply disconnected when the ligation procedure has been completed.

In one embodiment, an activating mechanism mounts to an endoscope by means of a mounting component which is inserted directly into a port of the endoscope. In this way, the activating mechanism can be securely and simply mounted to the endoscope with a single motion. In one specific embodiment, a mounting component is adapted to be fitted within an operating or working channel and/or within the operating channel's sealing port for a wide variety of endoscopes. In this manner, the secure attachment of the activating mechanism is simply accomplished for the ligating procedure to be conducted, and the mechanism can also be readily removed after the ligation has been performed.

In another aspect of the invention, there is further provided means for activating the ligating device which is precisely controllable and which can be simply disconnected upon the completion of the ligation procedure. In one embodiment, an activating component operates in a working mode in which the activation line can be retracted under precisely controlled tension to release the ligating bands as desired. When the procedure is suspended or completed, the activating component can be switched to a disengaged mode in which tension on the activation line is released to prevent unintended band release and to allow for easy disconnection of the activation line from the activating component.

It is an object of the present invention to provide an activating mechanism for an endoscopic ligator which easily mounts to an endoscope in a stable fashion. It is a further object of the present invention to provide an activating mechanism for an endoscope which can be securely mounted within a channel or auxiliary port of an endoscope.

It is a further object of the present invention to provide an activating mechanism for an endoscopic ligator which is precisely controllable to effectuate endoscopic ligation as desired. Yet another object is to provide such an activating mechanism which is convenient to use and which can be readily disconnected at the completion of the procedure.

These and other objects and advantages of the present invention will be apparent from a review of the following description of the preferred embodiment.

BRIEF DESCRIPTION OF THE DRAWINGS

FIG. 11B is a view of the activating mechanism of FIG. 2 after insertion into the proximal channel portion of FIG. 1B.

FIG. 11C is a view of the activating mechanism of FIG. 2 after insertion into the proximal channel portion of FIG. 1C.

DETAILED DESCRIPTION OF THE PREFERRED EMBODIMENT

Figure 1:
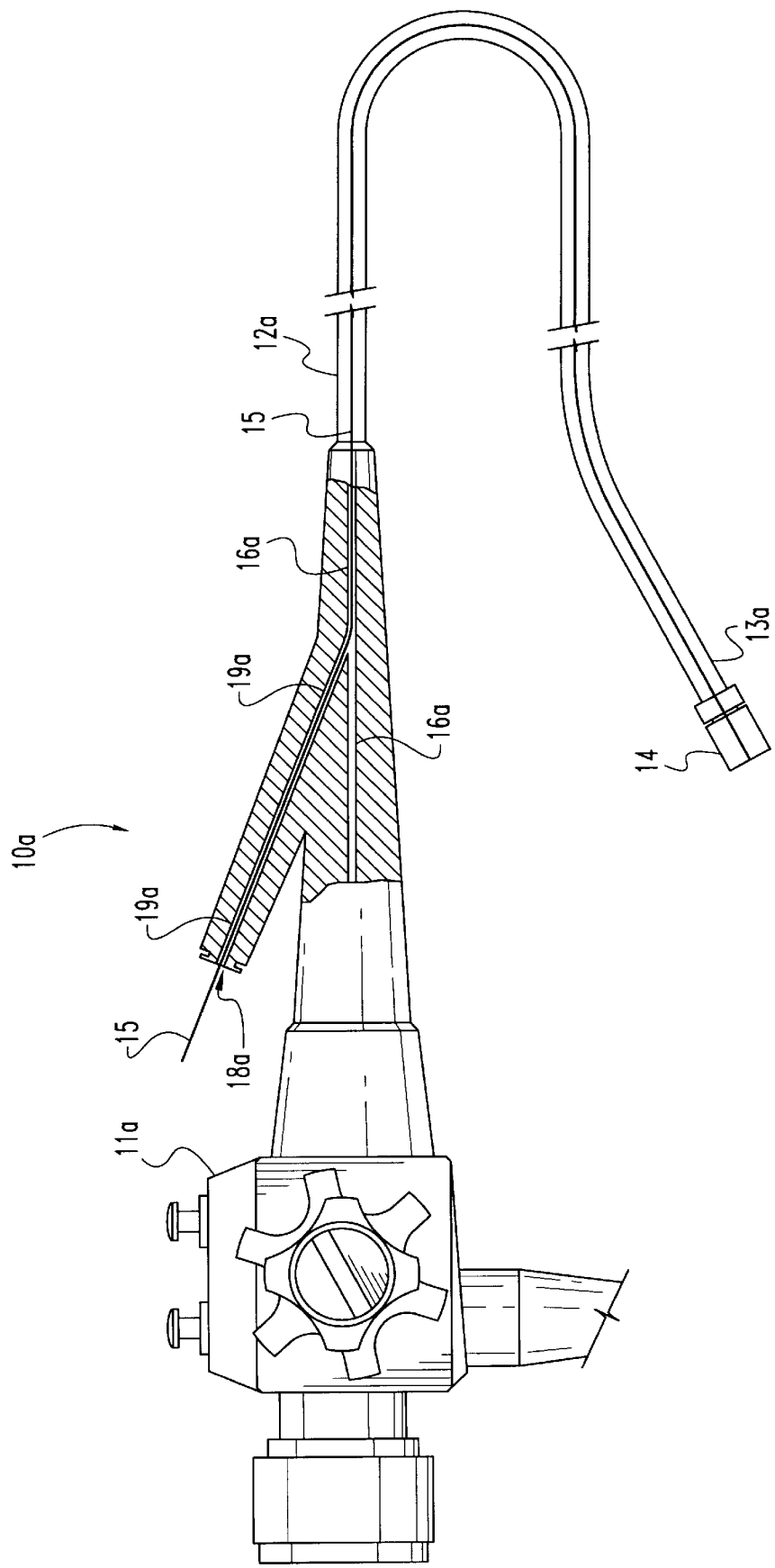
FIG. 1 is a longitudinal fragmented view of an endoscope with an endoscopic ligator (generally shown) that is located at the distal end of the endoscope.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring more particularly to the drawings, there is shown in FIG. 1 endoscope 10a with endoscopic ligator 14 attached to the distal or insertion end of endoscope 10a. Endoscopic ligator 14 is generally shown in FIG. 1. A more detailed description of one type of ligator 14 is shown in pending U.S. application Ser. No. 08/260,380 filed on Jun. 14, 1994. Specific reference is made to FIGS. 16–20 and descriptions thereof in the '380 Application, which disclosure is hereby incorporated by reference. The specification in co-pending U.S. application Ser. No. 08/709423, filed on Sep. 6, 1996 as a continuation-in-part of of the above application Ser. No. 08/260,380 and entitled Endoscopic Ligating Apparatus is incorporated herein by reference as well. In general terms, ligator 14 carries a number of ligation bands that can be individually or collectively released from the ligator around a subject tissue. The present invention can also be adapted for use with other ligators, such as the instrument in U.S. Pat. No. 5,320,630.

Endoscope 10a can be a conventional endoscope with an operating control portion 11a, a flexible section 12a, and a distal or insertion end portion 13a. Endoscopic ligator 14 is located at distal end portion 13a of endoscope 10a and includes an activation line 15. Endoscope 10a also includes an operating or working channel 16a which extends through endoscope 10a from distal end portion 13a to operating control portion 11a and to proximal opening 18a. Activation line 15 is preferably threaded from ligator 14 through operating channel 16a and exits through proximal opening 18a.

Figure 1A:
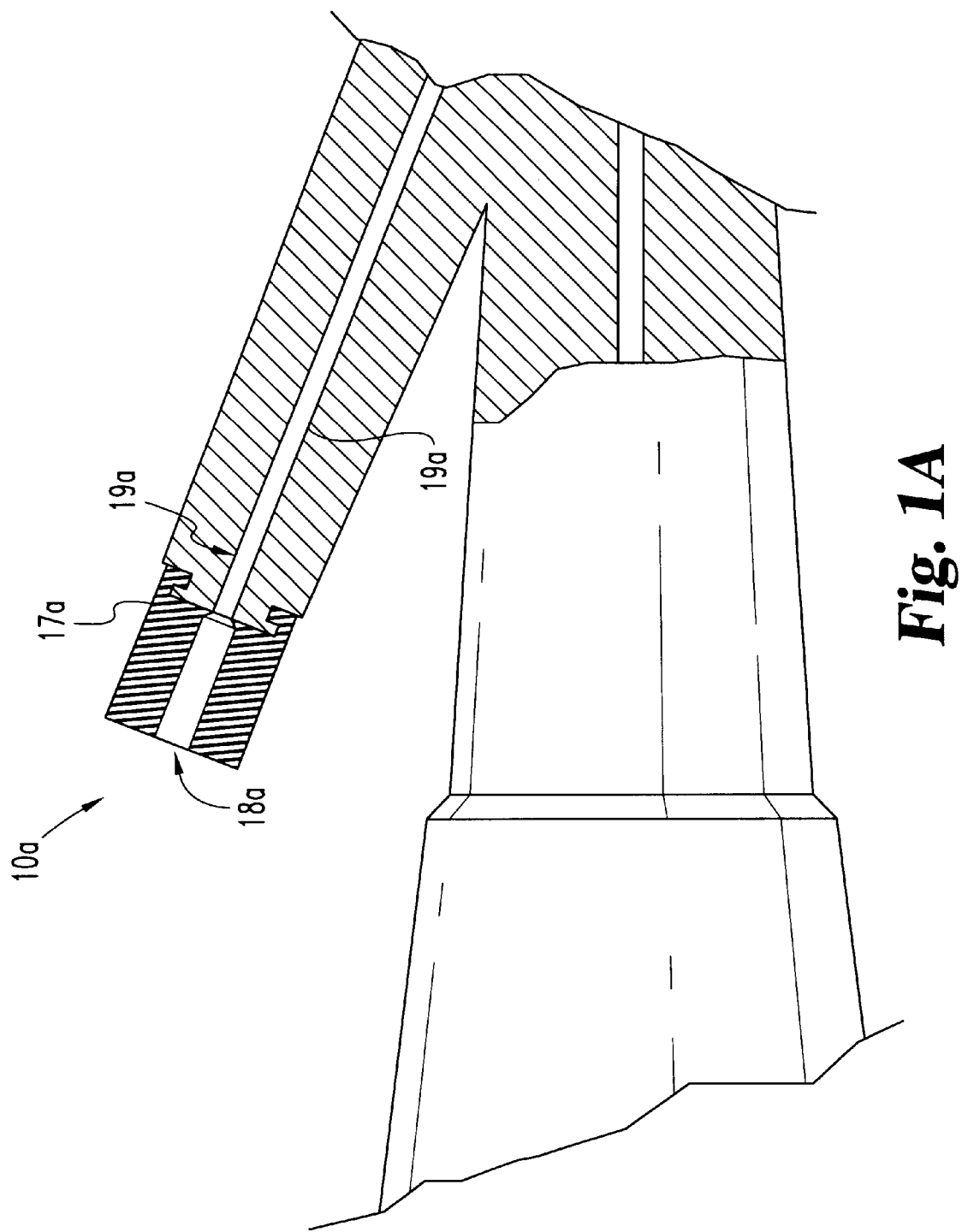
FIG. 1A is a cross-sectional view of a first configuration of a proximal channel portion of an operating channel of the endoscope of FIG. 1.
Figure 1B:
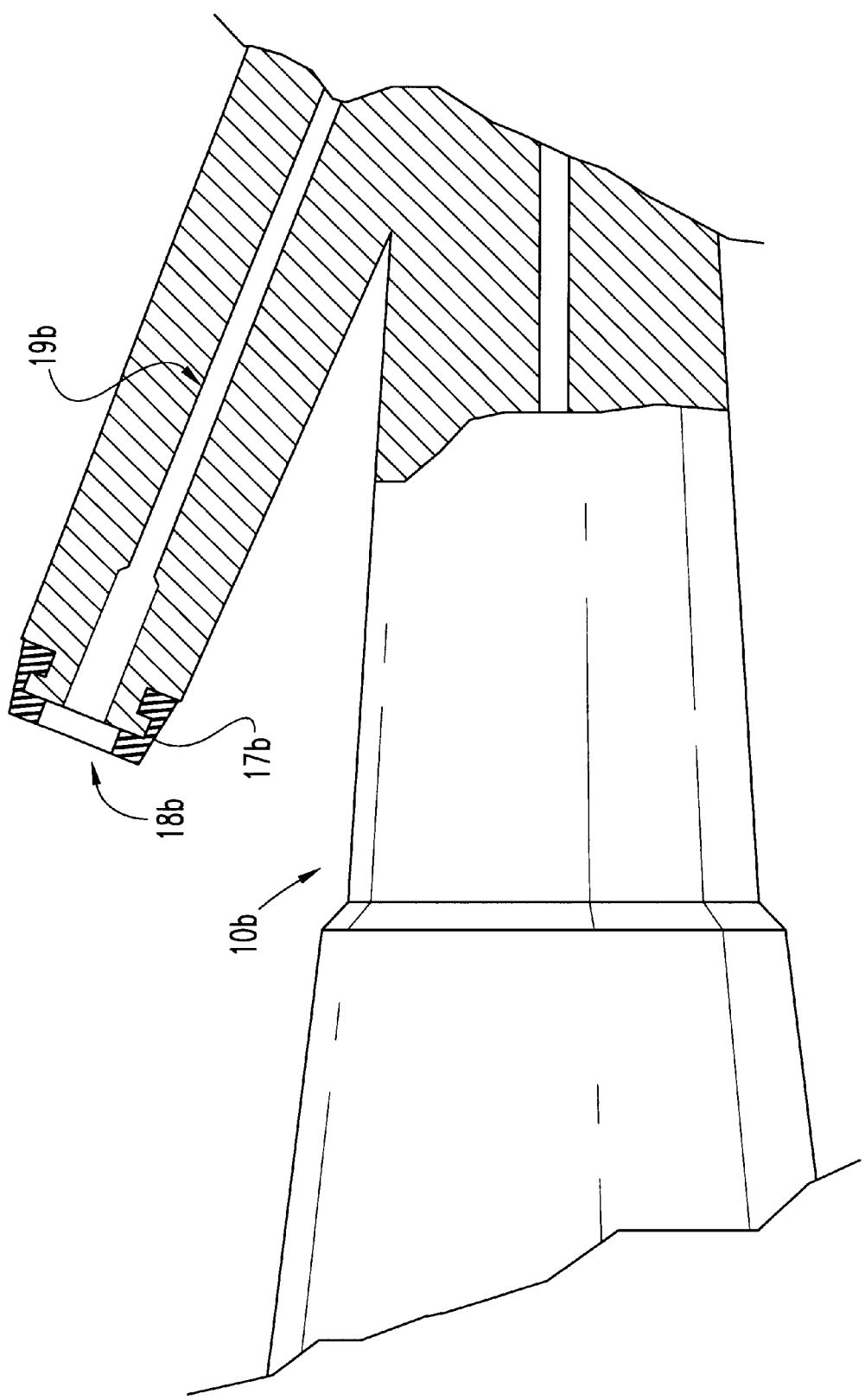
FIG. 1B is a cross-sectional view of a second configuration of the proximal channel portion of an operating channel of the endoscope of FIG. 1.
Figure 1C:
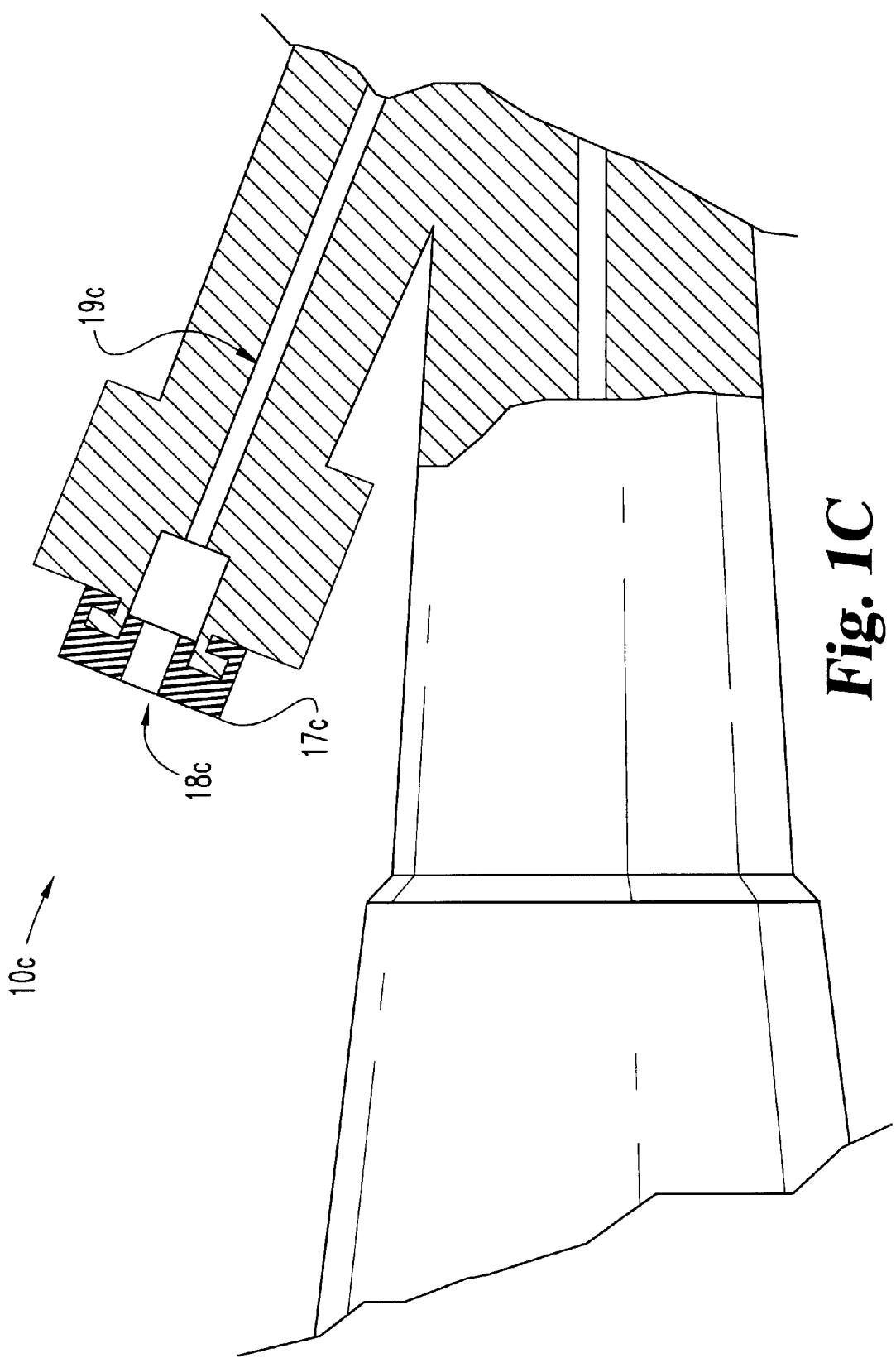
FIG. 1C is a cross-sectional view of a third configuration of the proximal channel portion of an operating channel of the endoscope of FIG. 1.

Referring still to FIG. 1, operating channel 16a includes a proximal channel portion 19a at the proximal opening 18a, which can be constructed in a variety of configurations. For example, FIGS. 1A, 1B and 1C are cross-sectional views of proximal channel portions 19a, 19b and 19c, respectively, each proximal channel portion having a different configuration. FIG. 1A shows endoscope 10a which is similar to a type of commercial endoscope generally sold by Pentax. FIG. 1B shows endoscope 10b which is similar to a type of commercial endoscope generally sold by Olympus. FIG. 1C shows endoscope 10c which is similar to a type of commercial endoscope generally sold by Fujinon. These endoscopes include sealing members 17a–c, respectively, mounted at the corresponding proximal channel portions 19a–c.

Figure 2:
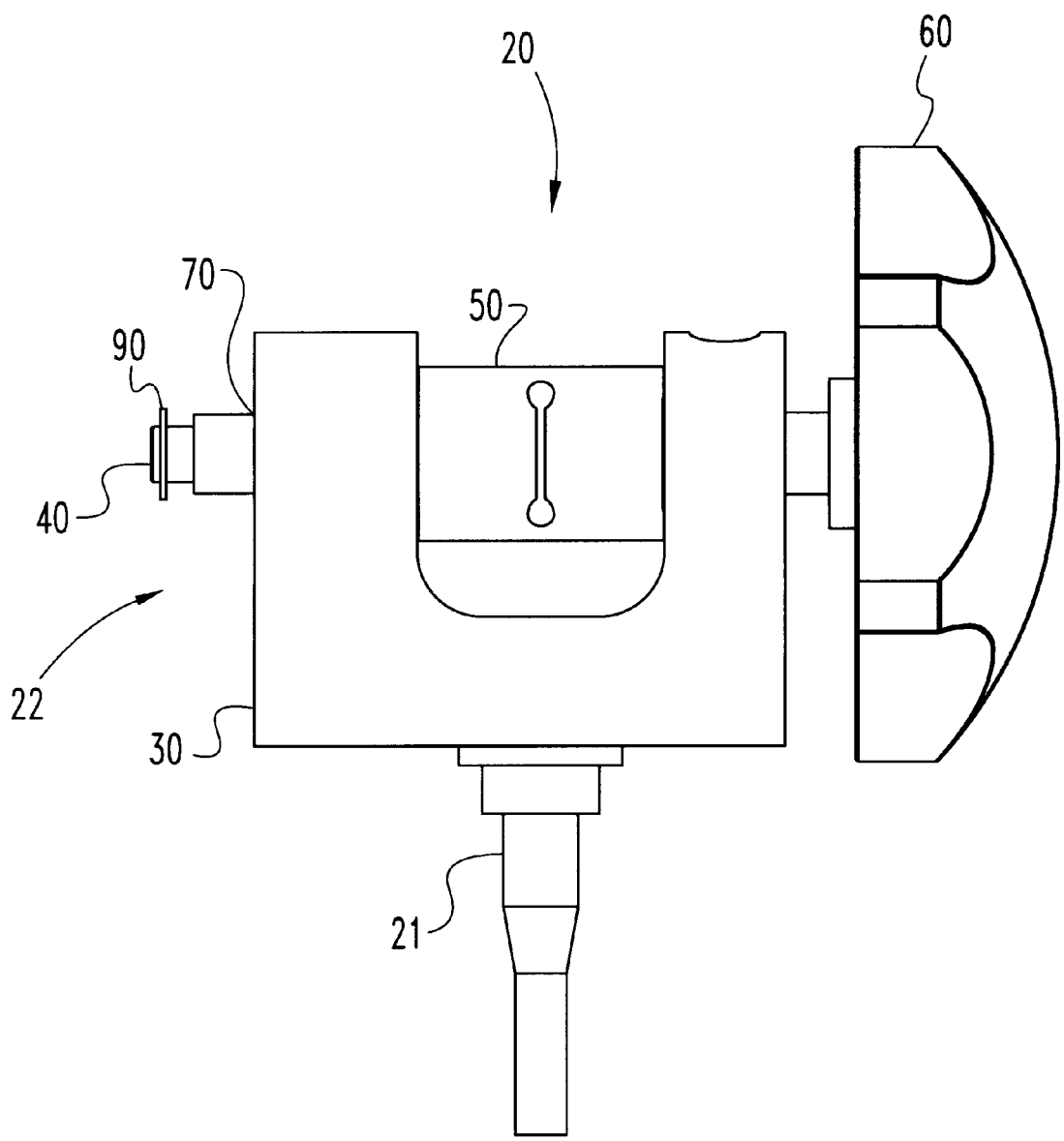
FIG. 2 is a top plan view of an activating mechanism for activating the endoscopic ligator of FIG. 1.

FIG. 2 is a top plan view of an activating mechanism 20 according to one embodiment of the present invention. Activating mechanism 20 includes mounting component 21 and activating component 22. Activating component 22 can include base 30, drive pin 40, spool 50, knob 60, roller clutch 70 (see FIG. 4B), and retaining cap 90. Mounting component 21 attaches to activating component 22 and is used to mount activating mechanism 20 to proximal channel portions 19a, 19b, 19c, or to other auxiliary port or proximal channel portion configurations of other endoscopes.

Figure 3A:
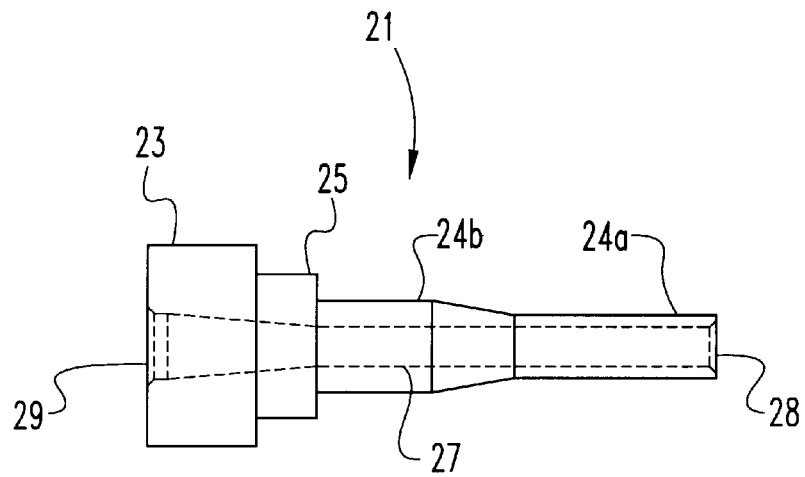
FIGS. 3A–3C are views of a mounting component of the activating mechanism of FIG. 2.

FIG. 3A is a view of a first embodiment of mounting component 21. Mounting component 21 includes coupling portion 23, first mating portion 24a, second mating portion 24b and outer sealing portion 25. Coupling portion 23 is adapted to be connected to activating component 22. Coupling portion 23, for example, can be threaded, or press-fit into, or integral with activating component 22.

The first, second and third mating portions 24a–c, respectively, and outer sealing portion 25 of mounting component 21 are particularly configured in one specific embodiment as shown in FIG. 3A. It is to be appreciated that mounting component 21 can be constructed in a variety of alternative configurations as well in accordance with the teachings of this invention.

The specific embodiment of the mounting component 21 shown in FIG. 3A can be engaged to an endoscope having a proximal opening 18a and proximal channel portion 19a as shown in FIG. 1A. In the depicted endoscope 10a, a sealing member 17a is provided at the proximal channel portion. The mounting component of FIG. 3A extends into proximal channel portion 19a through proximal opening 18a and sealing member 17a. In this specific embodiment, first mating portion 24a is shaped to be fitted within proximal channel portion 19a, while the second mating portion 24b is received within sealing member 17a. In this specific embodiment, the outer sealing portion 25 is not received within the sealing member 17a or proximal channel portion 19a of the endoscope.

The fit between the mating portion 24a–b of the mounting component and the sealing member 17a and proximal channel portion 19a of the endoscope provides a stable mount for the activating mechanism 20. Mounting component 21 is configured to fit in a variety of ways to serve to enhance the secure mounting of the device to various endoscopes. For example, depending on the endoscope with which the activating mechanism is being mounted, the fit may be a form fit in which the mounting component portion essentially follows the shape of the endoscope sealing member or proximal channel portion. The fit can also be a friction or a press fit or the length of the mounting component or a portion thereof, or alternatively, the mounting component portions could fit loosely within the endoscopic channel to provide enhanced stability by which the mounting component 21 restricts or limits relative movement of the activating mechanism 20 about the endoscopic operating channel.

The mounting component of FIG. 3A can be stably mounted to any of a variety of different endoscopes. In FIG. 1B, for example, first mating portion 24a and second mating portion 24b are sized to fit within proximal channel portion 19b of an endoscope which is differently design than that shown in FIG. 1A. With the same structure of the mounting component, the outer sealing portion 25 can be received within the sealing member 17b of the endoscope in FIG. 1B as well as the endoscope of FIG. 1A. As shown in further detail in FIGS. 10B and 11B, In FIG. 1B, the mating portions 24a–b are form or geometrically fitted within the proximal channel portion 19b. The outer sealing portion 25 is also preferably resiliently or form fitted into the sealing member 17b. As explained above, the mounting component portions are sized and configured to fit within the proximal channel portion 19b and/or sealing member 17b of variously designed endoscopes so as to help achieve a stable mounting of the device to the endoscope.

The mounting component of FIG. 3A can also be mounted, for example, to an endoscope of the type shown in FIG. 1C. Again, the fitting of mounting component 21 within the sealing member 17c and/or proximal channel portion 19c of the endoscope 10c can be accomplished in various ways which help to accomplish the stable mounting of activating mechanism 20. In this specific example, it is to be noted that outer sealing portion 25 is not configured to extend into the sealing member 17c, as is shown by the other above examples.

Figure 3B:
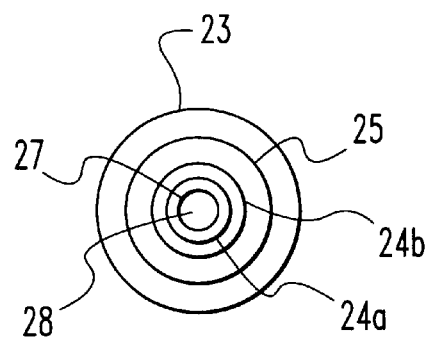
Figure 3C:
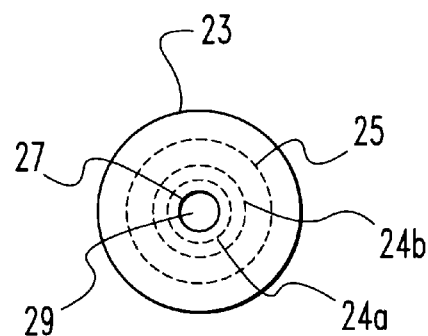

Mounting component 21 also preferably provides first threading channel 27 which extends through mounting component 21. First opening 28 of first threading channel 27 is shown in FIG. 3B and an opposite second opening 29 of first threading channel 27 is shown in FIG. 3C. After mounting component 21 has been inserted into a proximal channel portion configuration, activation line 15 can be threaded into first opening 28 and out of second opening 29 for connection to activating component 22.

Figure 4A:
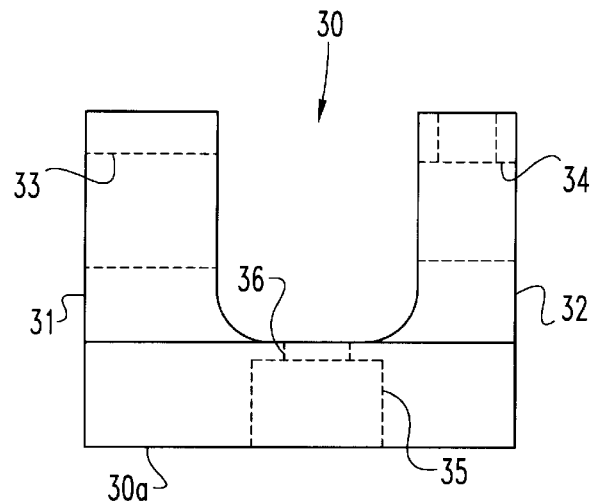
FIGS. 4A–4E are views of a base of the activating mechanism of FIG. 2.
Figure 4B:
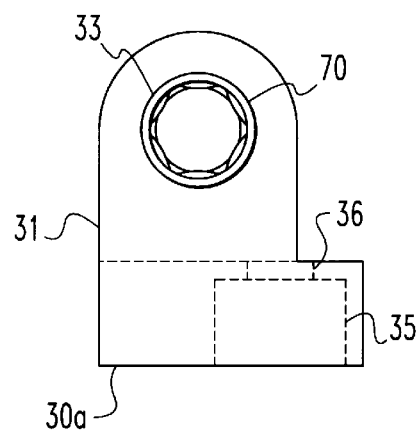
Figure 4C:
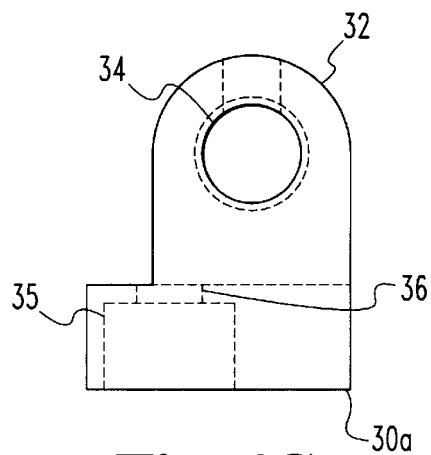
Figure 4D:
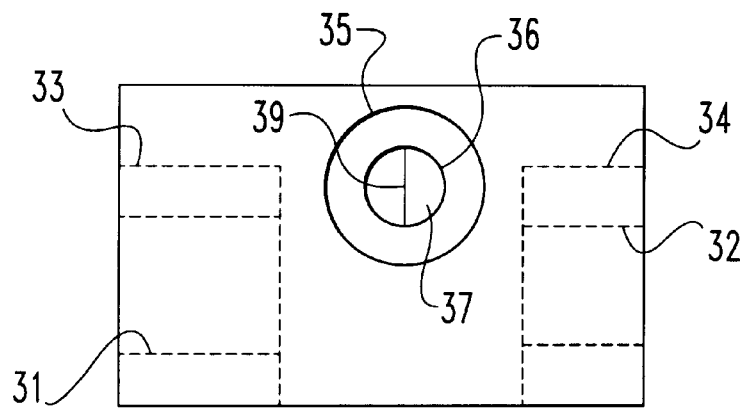
Figure 4E:
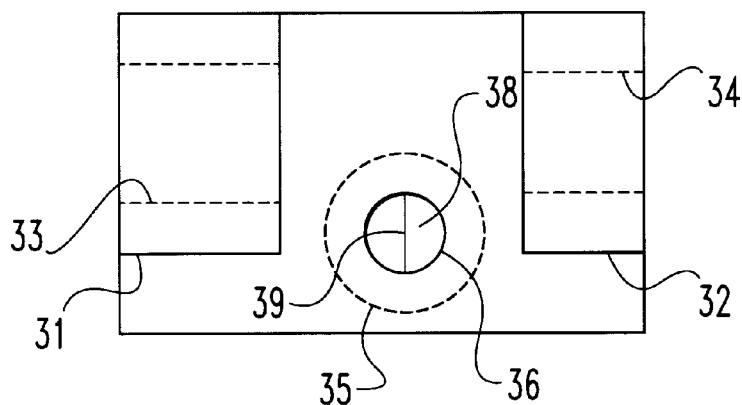

FIG. 4A is a frontal view of base 30 of activating component 22. Base 30 can include a base portion 30a, first arm 31 connected to base portion 30a, and a second arm 32 also connected to base portion 30a. While the present invention contemplates that the connections of first arm 31 and second arm 32 can exist in any form, preferably first arm 31 and second arm 32 are integral with base portion 30a. As shown in FIG. 4B, first arm 31 provides first receiving opening 33 and as shown in FIG. 4C, second arm 32 provides second receiving opening 34. Base portion 30a defines recess 35 located on its bottom side and second threading channel 36 which communicates between recess 35 and the top side of base portion 30a. FIG. 4D is a bottom side view of FIG. 4A, and further shows recess 35 and first opening 37 of second threading channel 36. FIG. 4E is a top side of FIG. 4A, showing the top side of first arm 31 and second arm 32, and second opening 38 of second threading channel 36 with an inner sealing member 39 located therein. When activation line 15 is threaded through mounting component 21, it is further threaded into first opening 37, through an inner sealing member 39 disposed within second opening 38, and out of second opening 38.

Figure 5A:
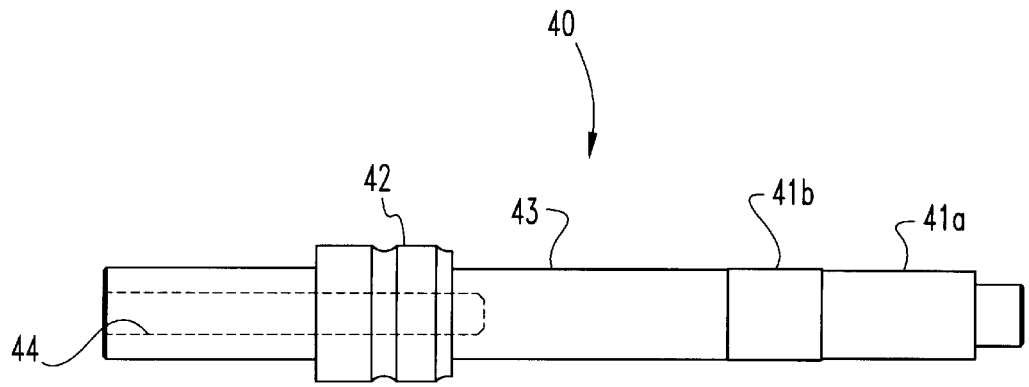
FIGS. 5A–5C are views of a drive pin of the activating mechanism of FIG. 2.
Figure 5B:
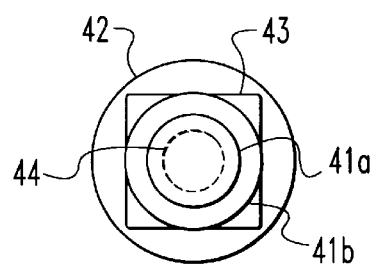
Figure 5C:
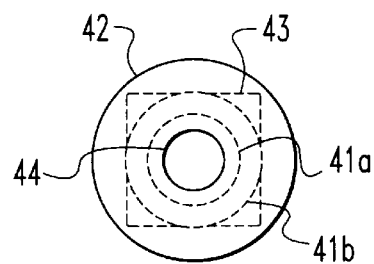

FIG. 5A is a side view of drive pin 40. Drive pin 40 preferably includes first rotating portion 41a, second rotating portion 41b, third rotating portion 42, and fourth rotating portion 43. Depending upon the mode of operation, first rotating portion 41a or second rotating portion 41b may be disposed within roller clutch 70 (see FIG. 4b) located within first receiving opening 33 of first arm 31. First rotating portion 41a is dimensioned to rotate within roller clutch 70 while second rotating portion 41b is dimensioned to engage roller clutch 70 within first receiving opening 33 of first arm 31 to thereby allow for rotation in only one direction when activating component is set in its engaged working mode. FIG. 5B is a front view of drive pin 40. First rotating portion 41a is configured to receive retaining cap 90 located on the end of drive pin 40 (see FIG. 2). Retaining cap 90 prevents the dislodging of first rotating portion 41a from first receiving opening 33. FIG. 5C is a back view of drive pin 40.

Referring back to FIG. 5A, third rotating portion 42 is disposed within second receiving opening 34 of second arm 32. Third rotating portion 42 is designed to rotate in and slide within second receiving opening 34. Drive pin 40 further includes a knurled portion 44 in third rotating portion 42 which connects to knob 60. Fourth rotating portion 43 is designed to be disposed within spool 50.

Figure 6A:
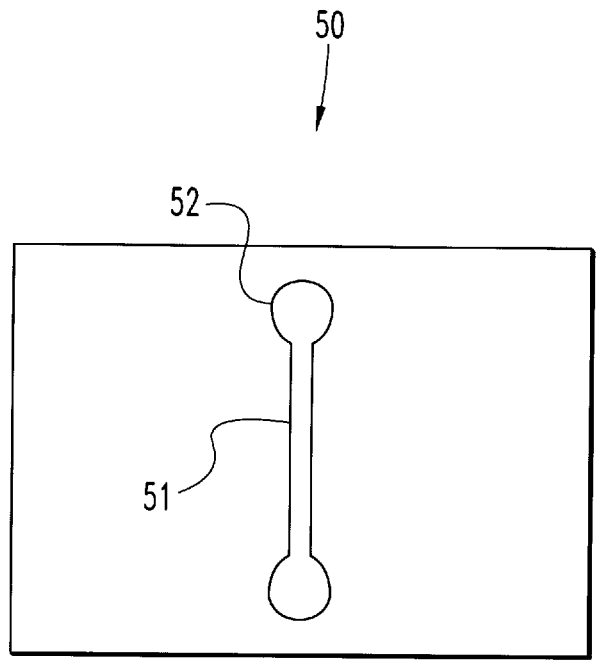
FIGS. 6A–6B are views of a spool of the activating mechanism of FIG. 2.
Figure 6B:
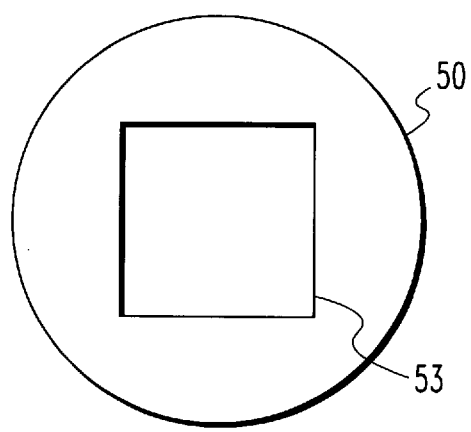

FIG. 6A is a side view of spool 50. Spool 50 can include a slot 51 having a hole 52. Hole 52 and slot 51 receive activation line 15 from second opening 38 of base 30. Activation line 15 is coupled to hole 52 and slot 51 by slipping activation line into slot 51 and placing a knot in activation line 15 through hole 52. FIG. 6B is a front view of spool 50. Spool 50 further includes drive channel 53. Drive channel 53 receives third rotating portion 43 of drive pin 40 both of which can have a square cross-sectional shape as illustrated. Spool 50 thus rotates in the same direction as drive pin 40 when the drive pin 40 is rotated by knob 60, owing to the engagement between fourth rotating portion 43 of drive pin 40 and drive channel 53 of spool 50. It is understood that fourth rotating portion 43 of drive pin 40 and drive channel 53 of spool 50 can assume a variety of configurations provided that the spool 50 will rotate with drive pin 40.

Figure 7:
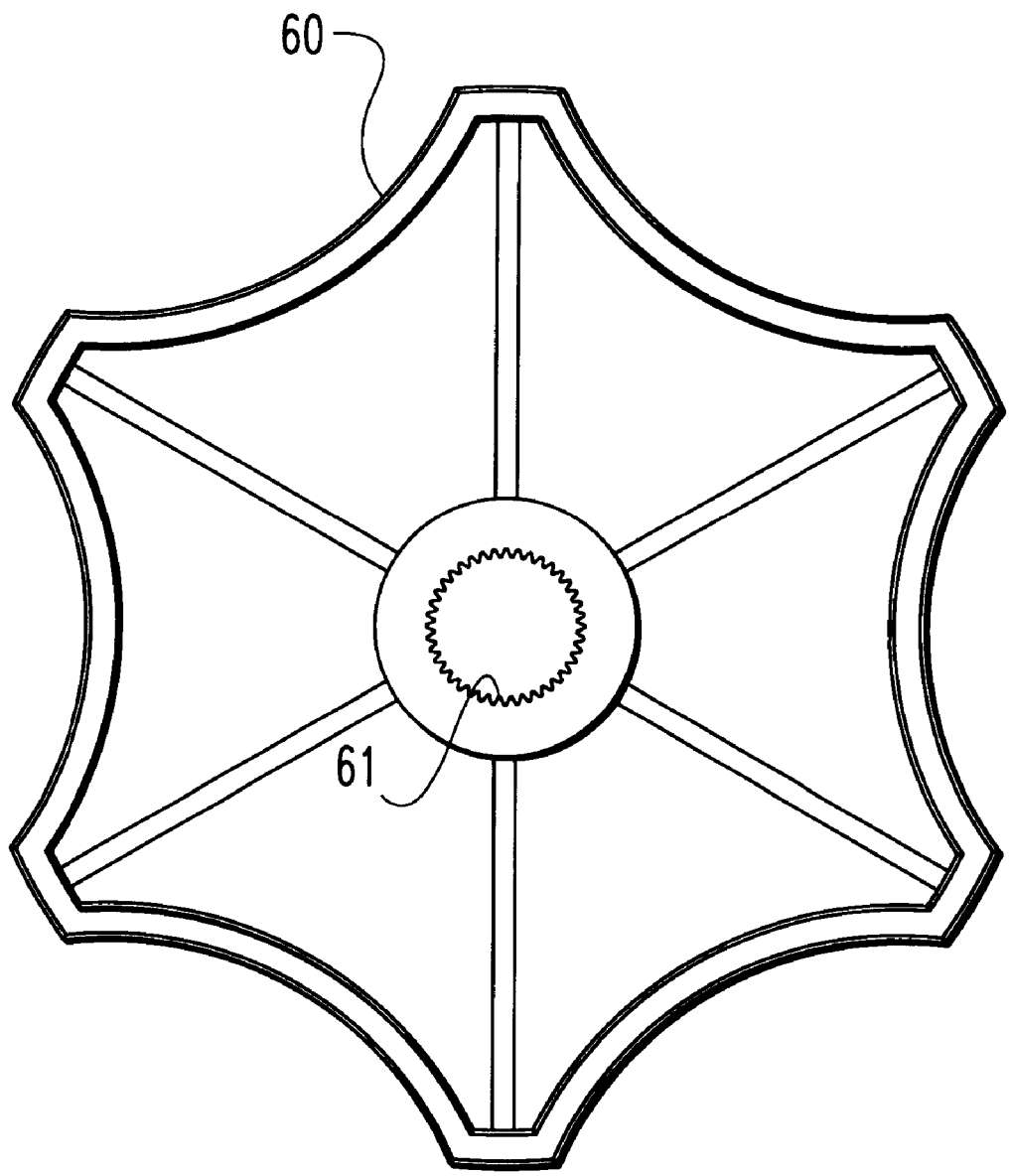
FIG. 7 is a view of a knob of the activating mechanism of FIG. 2.

FIG. 7 is a bottom side view of knob 60. Knob 60 includes connecting recess 61. Connecting recess 61 connects with drive pin 40 by fitting onto knurled portion of drive pin 40 (not shown). This connection enables knob 60 to rotate drive pin 40. The connection also prevents third rotating portion 42 of drive pin 40 from dislodging out of second receiving opening 34. The present invention contemplates that knob 60 can be operated either manually or mechanically.

Figure 8A:
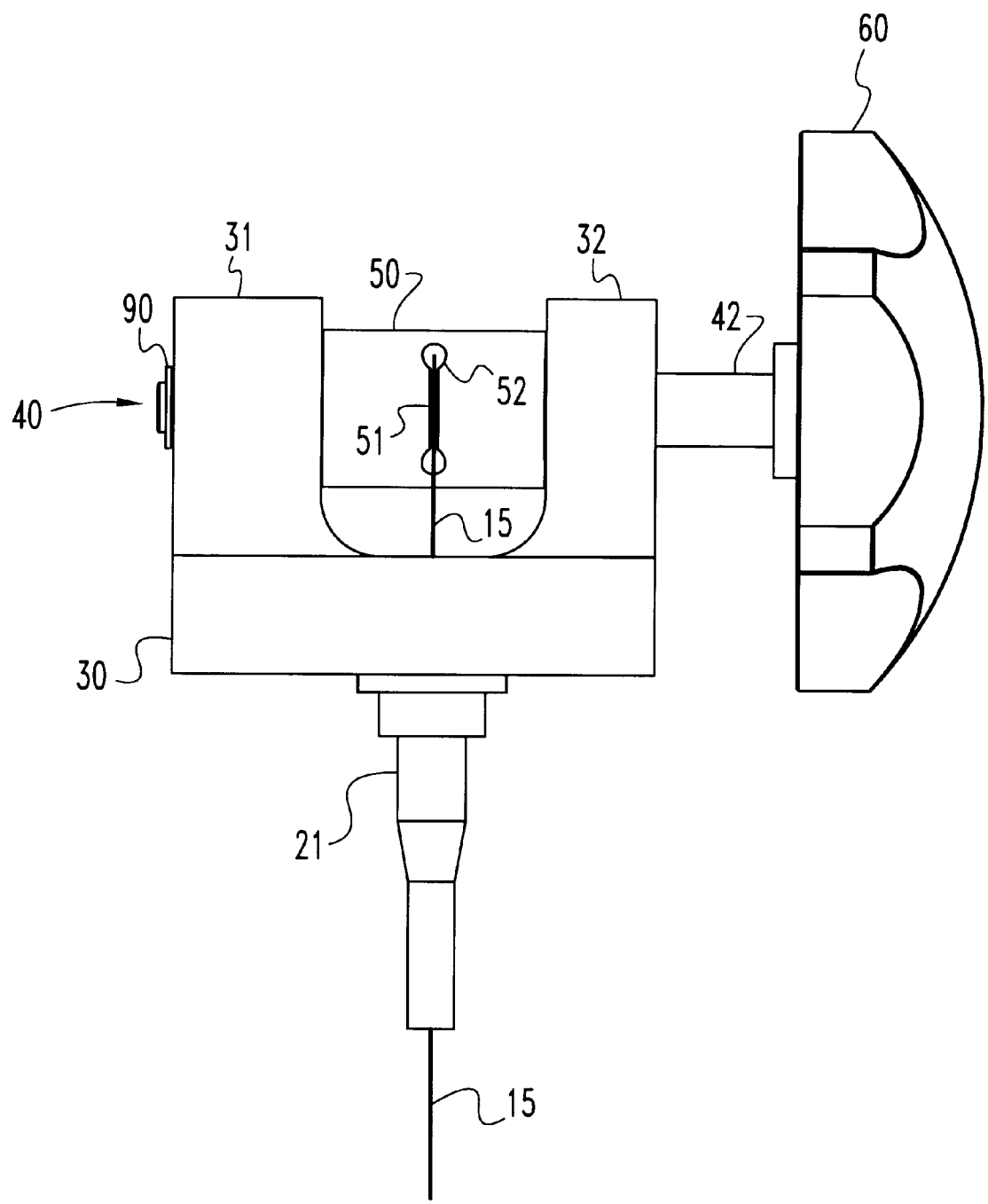
FIGS. 8A–8B are views of a disengaged mode of operation of the activating mechanism of FIG. 2 wherein knob 60 is free to rotate in either direction (A or B).
Figure 8B:
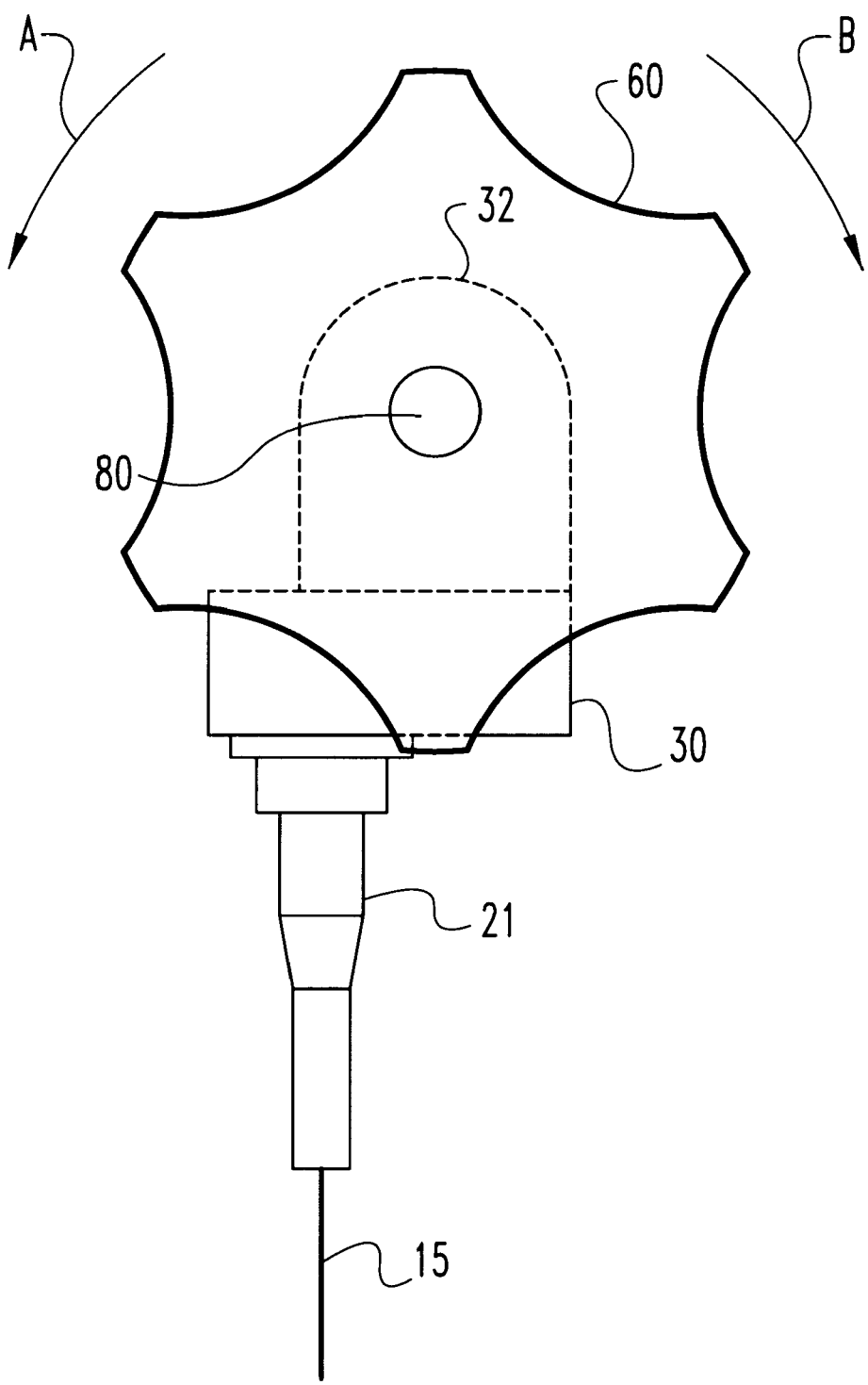

FIGS. 8 and 9 are views of the two modes of operation for activating mechanism 20. FIG. 8A depicts the disengaged mode of operation. Activation line 15 is threaded through mounting component 21 and base 30, and is coupled to spool 50. The disengaged mode of operation is based on a disengaged position of drive pin 40 within roller clutch 70. FIG. 8A depicts third rotating portion 42 of drive pin 40 being substantially disposed outside of second arm 32. FIG. 8A further shows first rotating portion 41a of drive pin 40 being substantially disposed within first arm 31. In this position, first rotating portion 41a is within the one-way roller clutch 70. This is the disengaged position of drive pin 40. As shown in FIG. 8B, when drive pin 40 is in the disengaged position, knob 60 can be rotated freely in either direction (A or B). After the attachment of activation line 15 to spool 50, knob 60 can be rotated to wrap activation line 15 around spool 50. To unwrap activation line 15, knob 60 can be rotated in the opposite direction of the first rotation.

Figure 9A:
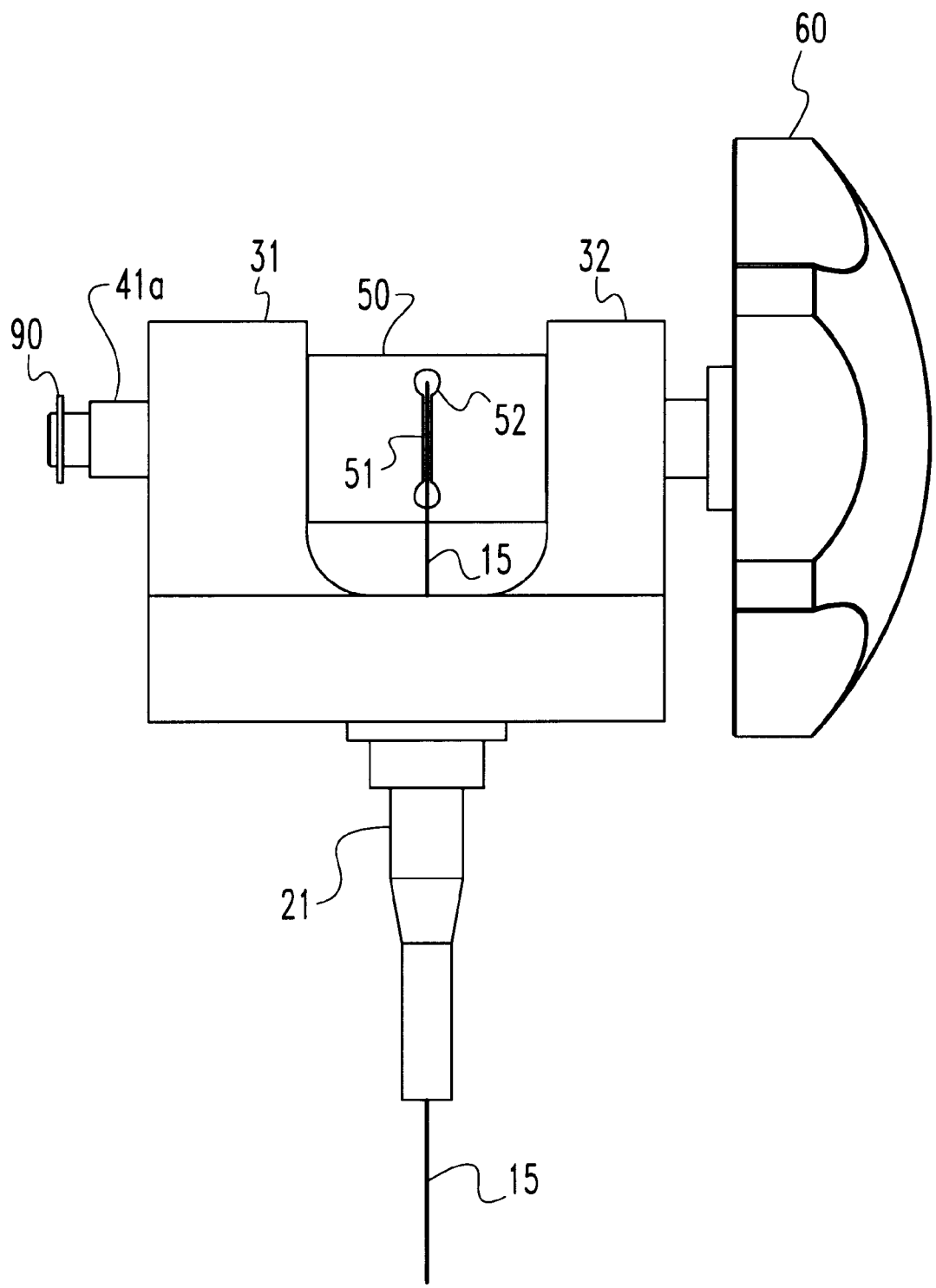
FIGS. 9A–9B are views of a working mode of operation of the activating mechanism of FIG. 2 wherein knob 60 is only free to rotate in a single direction.
Figure 9B:
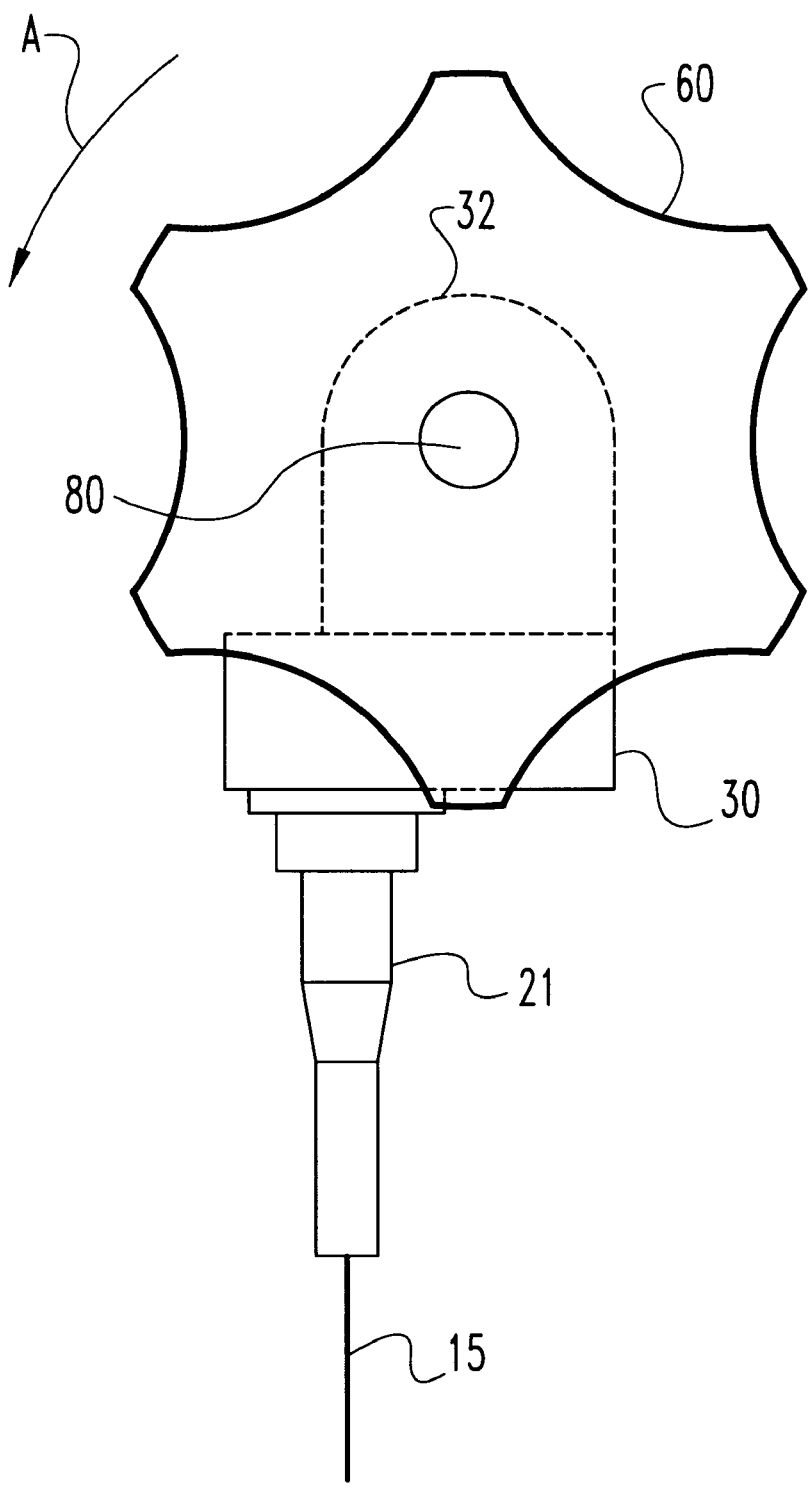

FIG. 9A depicts the working mode of operation. The working mode of operation is also based on a working position of drive pin 40 within roller clutch 70. FIG. 9A shows the second rotating portion segment 42 being substantially disposed within second arm 32. FIG. 9A further shows first rotating portion 41a being substantially disposed outside of first arm 31 with second rotating portion 41b in engaging contact with roller clutch 70. As shown in FIG. 9B, when drive pin 40 is in the engaged position, knob 60 can only be rotated in one direction due to the engagement between second rotating portion 41b and clutch 70. After the attachment of activation line 15 to spool 50, knob 60 can be rotated in one direction to wrap activation line 15 around the spool 50 under controlled tension to release ligating bands from ligator 14 as desired. Upon completion of the procedure, activating component 21 may be reset in the disengaged mode to release the tension from activation line 15 and allow activation line 15 to be unwound from spool 50 and disconnected therefrom.

While two modes of operation has been described herein for activating mechanism 20, activating mechanism 20 could less desirably be used exclusively in a working mode, with roller clutch 70 and second rotating portion 41b being maintained in engagement. In a less preferred embodiment, roller clutch 70 could be eliminated and an element, such as a one-way clip, could be used to engage the drive pin 40, spool 50 and/or knob 60 to restrict the rotation of knob in only one direction as illustrated in FIG. 9B.

Figure 10A:
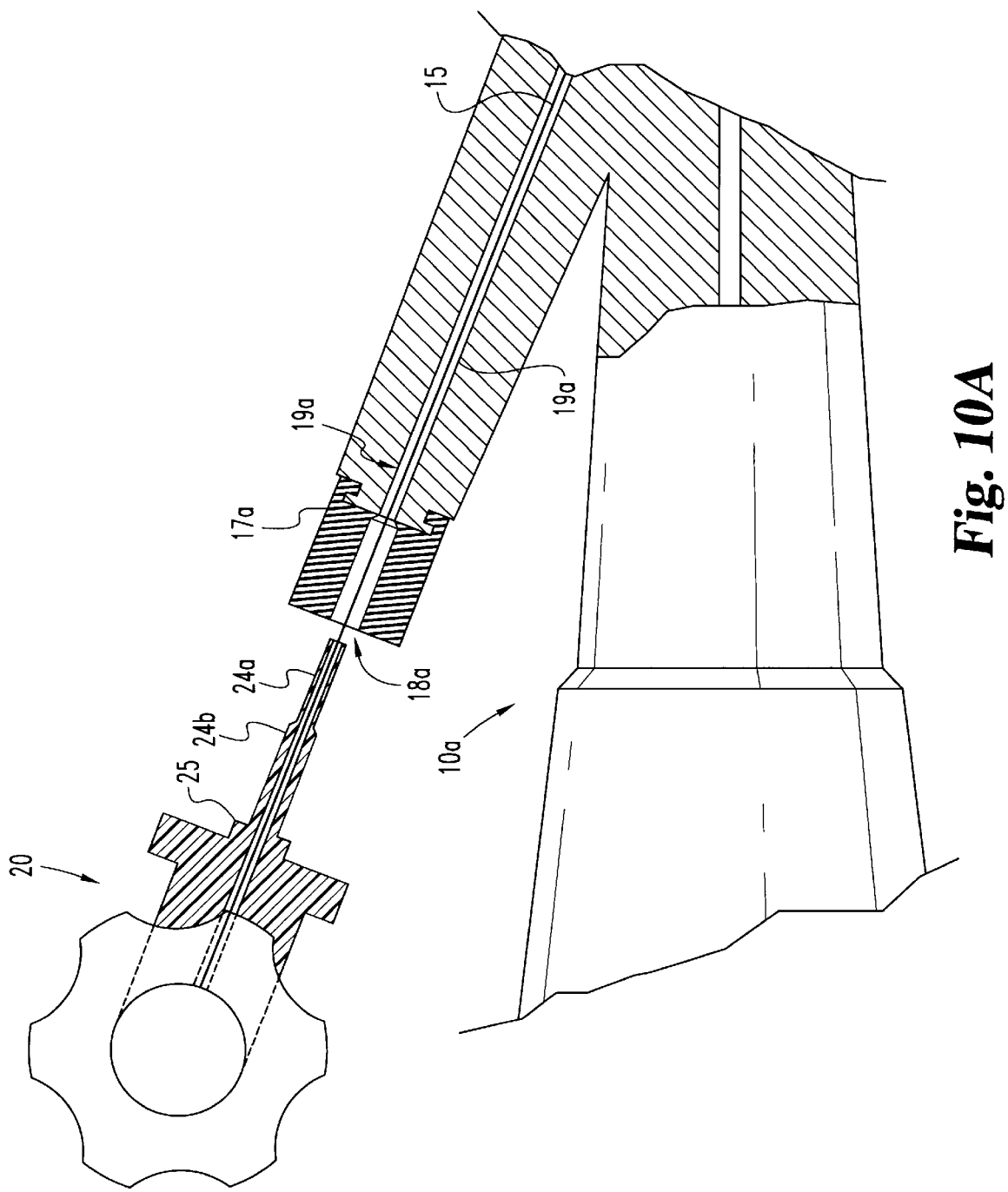
FIG. 10A is a view of the activating mechanism of FIG. 2 prior to insertion into the proximal channel portion of FIG. 1A.
Figure 11A:
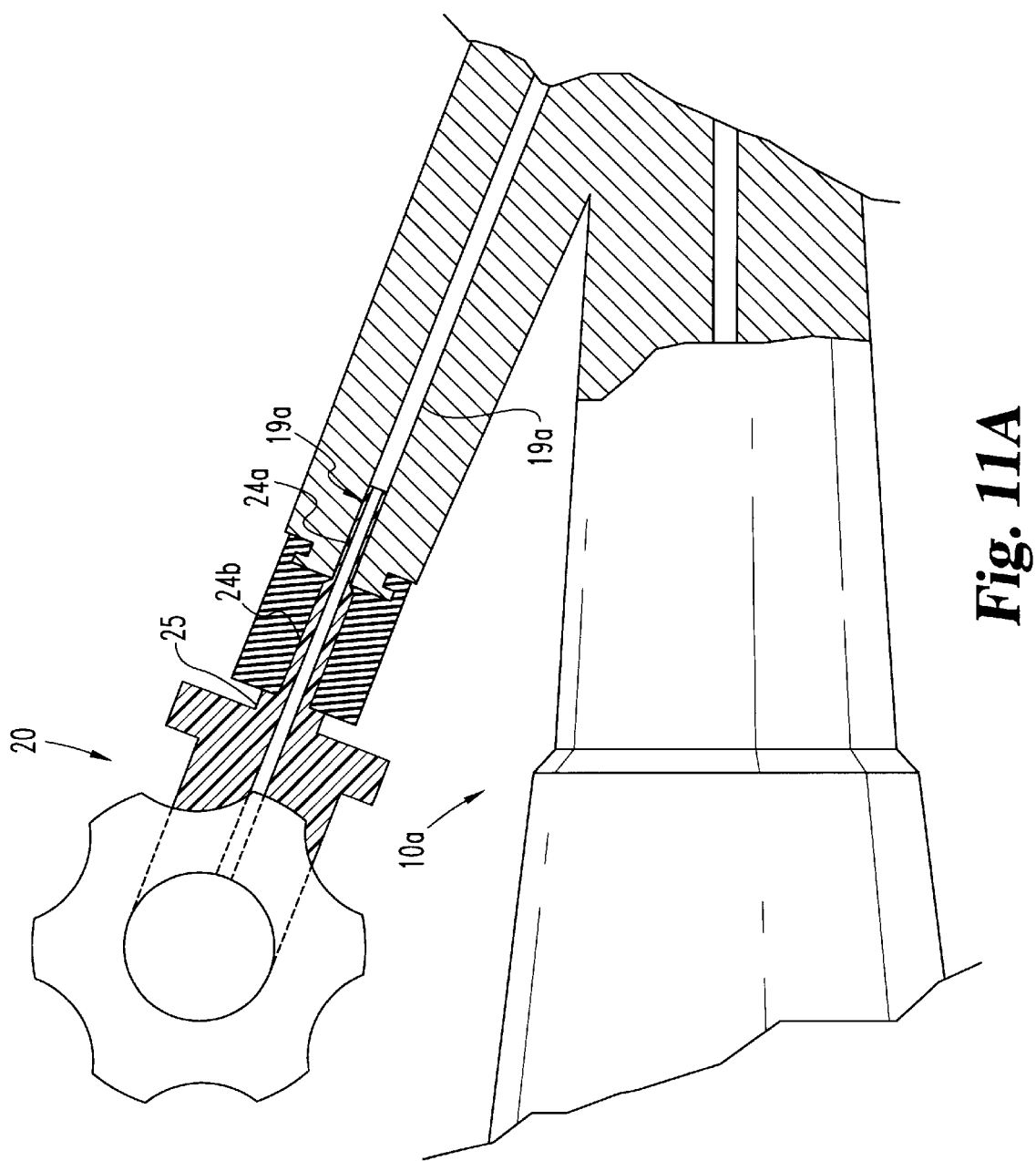
FIG. 11A is a view of the activating mechanism of FIG. 2 after insertion into the proximal channel portion of FIG. 1A.

FIGS. 10A and 11A show how activating mechanism 20 is mounted to endoscope 10a of FIG. 1A by inserting mounting component 21 into proximal channel portion 19a. For this illustration, endoscope 10a is shown provided with sealing member 17a which is coupled to proximal opening 18a. FIG. 10A shows the alignment of activating mechanism 20 with proximal opening 18a prior to insertion of mounting component 21 therein. FIG. 11A shows mounting component 21 inserted into proximal channel portion 19a. Upon insertion, first mating portion 24a and second mating portion 24b can achieve the fit within proximal channel portion 19a and sealing member 17a, correspondingly, as described above in order to mount activating mechanism 20 to endoscope 10a. As previously described, activation line 15 is threaded into and attached to activating mechanism 20.

Figure 10B:
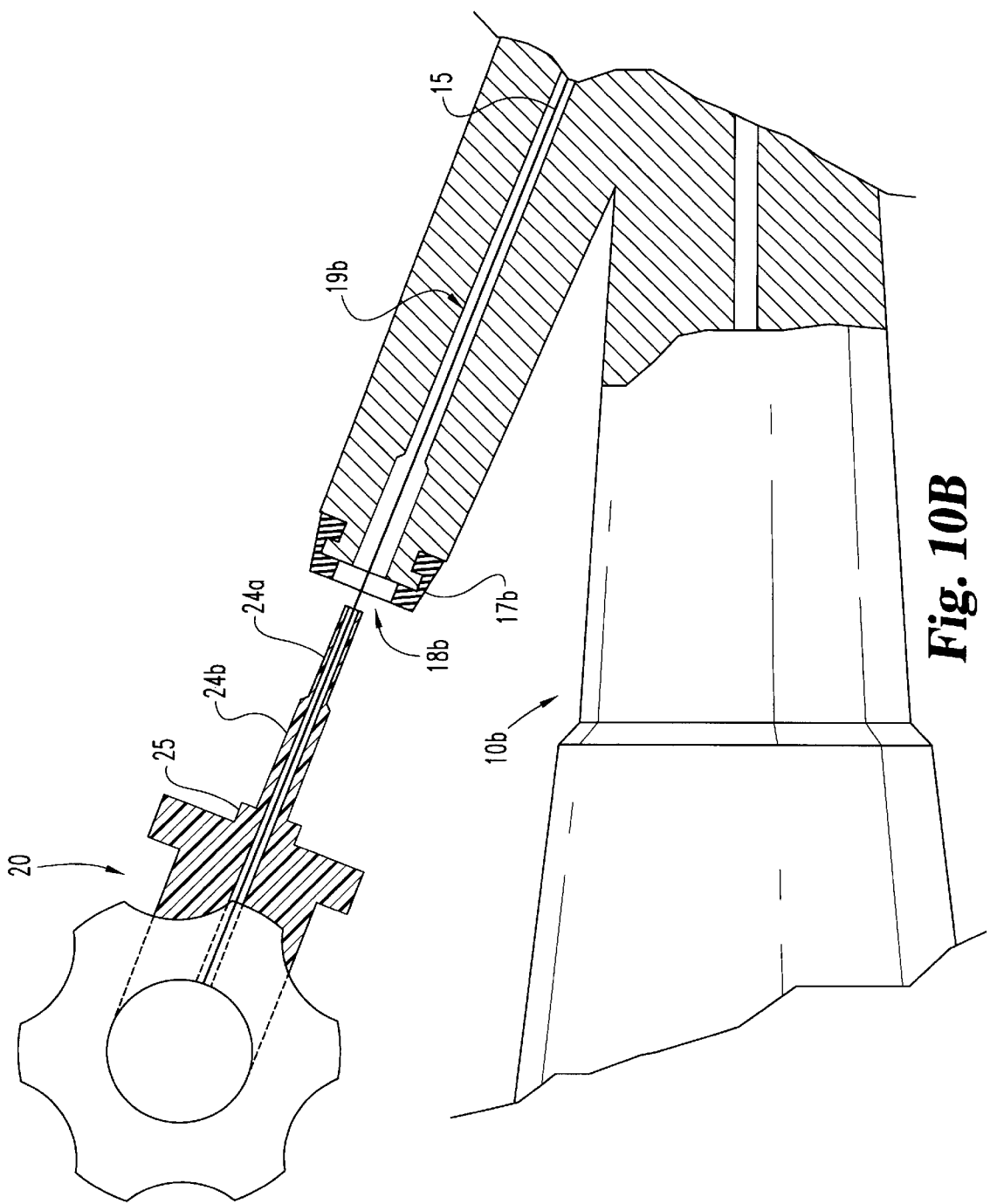
FIG. 10B is a view of the activating mechanism of FIG. 2 prior to insertion into the proximal channel portion of FIG. 1C.

FIGS. 10B and 11B show how activating mechanism 20 is mounted to endoscope 10b of FIG. 1B by inserting mounting component 21 into proximal channel portion 19b. For this illustration, endoscope 10b is shown provided with sealing member 17b which is coupled to proximal opening 18a. FIG. 10B shows the alignment of activating mechanism 20 with proximal opening 18b prior to insertion of mounting component 21 therein. FIG. 11B shows mounting component 21 inserted into proximal channel portion 19b. The fit between the first and second mating portions 24a–b and the proximal channel portion 19b, and between outer sealing portion 25 and sealing member 17b, can be as described above in order to mount activating mechanism 20 to endoscope 10b and outer sealing portion 25 seals with sealing member 17b of endoscope 10b.

Figure 10C:
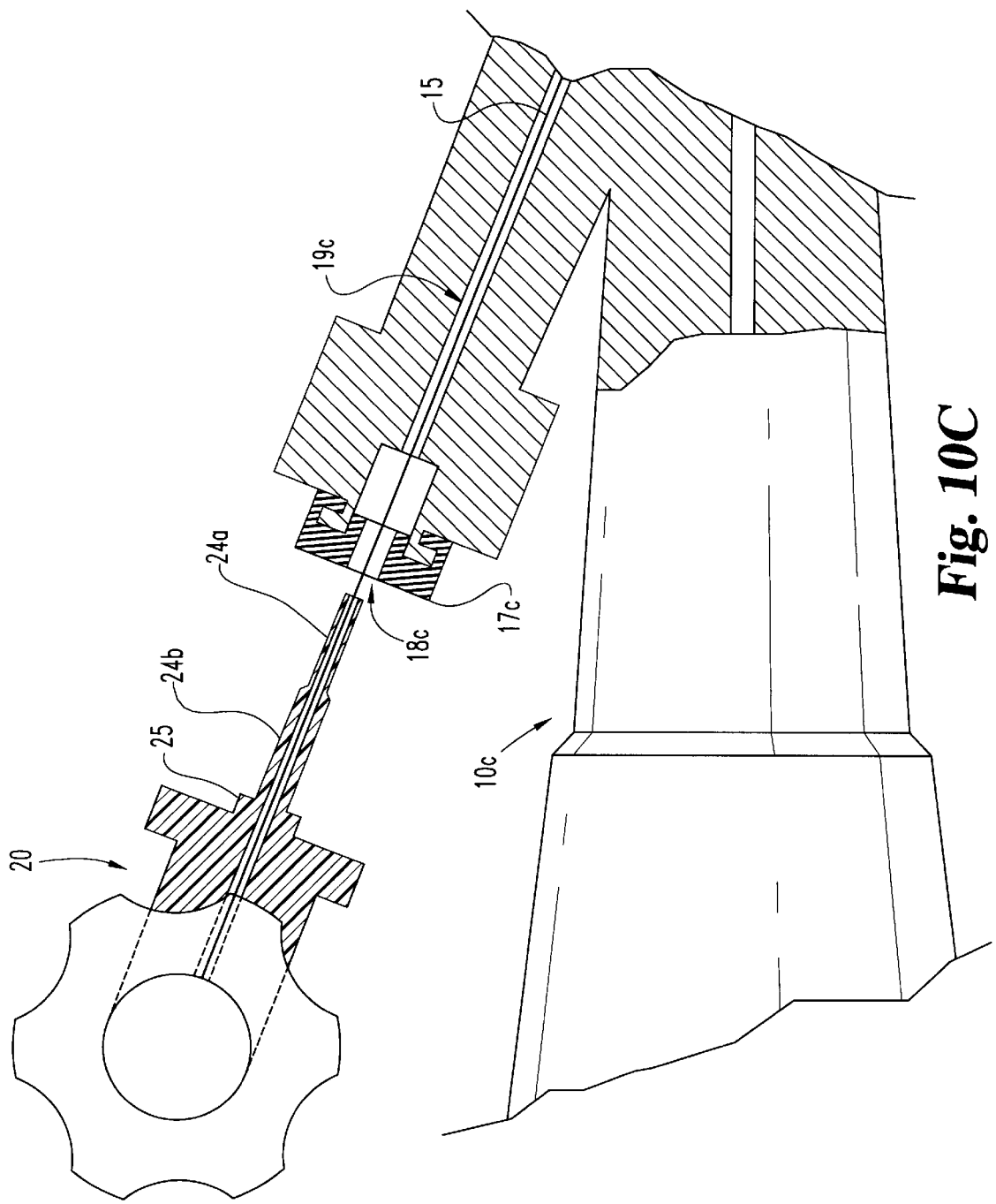
FIG. 10C is a view of the activating mechanism of FIG. 2 prior to insertion into the proximal channel portion of FIG. 1C.

FIGS. 10C and 11C show how activating mechanism 20 is mounted to endoscope 10c of FIG. 1C by inserting mounting component 21 into proximal channel portion 19c. For this illustration, endoscope 10c is shown provided with sealing member 17c which is coupled to proximal opening 18c. FIG. 10C shows the alignment of activating mechanism 20 with proximal opening 18c prior to insertion of mounting component 21 therein. FIG. 11C shows mounting component 21 inserted into proximal channel portion 19c. Again, the fit between the mounting component 21 and the proximal channel portion 19c and sealing member 17c can be as described above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An activating mechanism for activating an endoscopic ligator to ligate lesions within a hollow body organ, the endoscopic ligator being positioned at the distal insertion end of an endoscope, the endoscope having a channel which extends through the endoscope from an opening at the distal end to an opening at a proximal end of the endoscope, the ligator having an activation line which is threaded through the channel of the endoscope to the proximal opening of the endoscope, said activating mechanism comprising:

(a) a mounting component, said mounting component having a first portion sized to be inserted into the proximal opening of the channel of the endoscope, said mounting component including a threading channel extending therethrough for threading the activation line through said mounting component when said first portion of said mounting component is inserted into the proximal opening of the channel of the endoscope; and (b) an activating component connected to said mounting component, said activating component including means for attachment of the activation line when the activation line is threaded through said threading channel of said mounting component, and means for retracting the activation line when the activation line is attached to said activating component whereby the ligating device can be activated as desired by selective retraction of the activation line.

2. The activating mechanism of claim 1 in which the endoscope further includes a sealing member disposed over the proximal opening of the channel, the sealing member having an opening in communication with the proximal opening of the endoscope, wherein:

said mounting component further includes a second portion adjacent said first portion, said second portion sized to be received within the sealing member opening when said first portion extends through the proximal opening of the channel.

3. The activating mechanism of claim 2 wherein said second portion of said mounting component is sized to form a friction fit with the sealing member opening.

4. The activating mechanism of claim 1, wherein said attachment means includes a spool with means for engaging the proximal end of the activation line when the activation line is threaded through said threading channel of said mounting component;

wherein said retracting means includes
a knob operationally connected to said spool for manual rotation of said spool, and
a base configured to rotationally support said spool, said base defining an opening therethrough; and wherein said mounting component further includes a coupling portion sized to be received within said opening in said base to connect said activating component to said mounting component.

5. The activating mechanism of claim 1, wherein said attachment means includes a spool with means for engaging the proximal end of the activation line when the activation line is threaded through said threading channel of said mounting component; and wherein said retracting means includes
a knob operationally connected to said spool for manual rotation of said spool,
a base configured to rotationally support said spool, and
a one-way clutch engaging said spool to prevent rotation of said spool in one direction and permit rotation of said spool in an opposite direction.

6. The activating mechanism of claim 5, wherein said retracting means further includes a drive pin supported on said base to rotate and reciprocate relative to said base, said drive pin having a first portion disposed within said spool, said first portion of said drive pin having means for imparting rotational movement from said drive pin to said spool, a second portion connected to said knob, a third portion configured to engage said clutch when said drive pin is in a first position, said first position being said third portion disposed within said clutch, and a fourth portion adjacent said third portion, said fourth portion configured for free-wheel rotation within said clutch when said drive pin is reciprocated to a second position, said second position being said fourth portion disposed within said clutch.

7. An activating mechanism for activating an endoscopic ligator to ligate lesions within a hollow body organ, the endoscopic ligator being positioned at the distal insertion end of an endoscope, the endoscope having a channel which extends through the endoscope from an opening at the distal end to an opening at the proximal end of the endoscope, the ligator having an activation line which is threaded through the channel of the endoscope to the proximal opening of the endoscope, said activating mechanism comprising:

(a) a mounting component, said mounting component having a first portion sized to be inserted into the proximal opening of the channel of the endoscope, said mounting component including a threading channel extending therethrough for threading the activation line through said mounting component when said first portion is inserted into the proximal opening of the channel of the endoscope; and (b) an activating component connected to said mounting component, said activating component including
a spool to engage the proximal end of the activation line when the activation line is threaded through said threading channel of said mounting component, and
a knob operatively connected to said spool to manually rotate said spool whereby the activation line can be selectively retracted when engaged with said spool to activate the ligating device as desired.

8. The activating mechanism of claim 7 wherein said first portion of said mounting component is sized to form a friction fit within the channel of the endoscope.

9. The activating mechanism of claim 7 in which the endoscope further includes a sealing member disposed over the proximal opening of the channel, the sealing member having an opening in communication with the proximal opening of the endoscope, wherein:

said mounting component includes a second portion adjacent said first portion, said second portion sized to be received within the sealing member opening when said first portion extends through the proximal opening of the channel.

10. The activating mechanism of claim 9 wherein said second portion of said mounting component is sized to form a friction fit with the sealing member opening.

11. The activating mechanism of claim 7,
wherein said activating component further includes a based configured to rotationally support said spool, said base defining an opening therethrough; and
wherein said mounting component further has a coupling portion sized to be received within said opening in said base to connect said activating component to said mounting component.

12. The activating mechanism of claim 7, wherein said activating component further includes
a base configured to rotationally support said spool, and
a one-way clutch engaging said spool to prevent rotation of said spool in one direction and permit rotation of said spool in an opposite direction.

13. The activating mechanism of claim 12, wherein said activating component further includes a drive pin supported on said base to rotate and reciprocate relative to said base, said drive pin having
a first portion disposed with said spool, said first portion of said drive pin having means for imparting rotational movement of said drive pin to said spool,
a second portion connected to said knob,
a third portion configured to engage said clutch when said drive pin is in a first position, said first position being said third portion disposed within said clutch, and
a fourth portion adjacent said third portion, said fourth portion configured for free-wheel rotation within said clutch when said drive pin is reciprocated to a second position, said second position being said fourth portion disposed within said clutch.

* * * * *